US00PP23296P2

(12) United States Plant Patent
Bernuetz

(10) Patent No.: US PP23,296 P2
(45) Date of Patent: Jan. 1, 2013

(54) ***EUPHORBIA* PLANT NAMED 'BONPRIHO'**

(50) Latin Name: ***Euphorbia pulcherrima* Willd. ex Klotzsch×*Euphorbia cornastra***
Varietal Denomination: Bonpriho

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 13/136,895

(22) Filed: Aug. 12, 2011

(51) Int. Cl.
*A01H 5/00* (2006.01)

(52) U.S. Cl. ..... Plt./302

(58) Field of Classification Search ..... Plt./302, Plt./304
See application file for complete search history.

*Primary Examiner* — Kent L Bell
(74) *Attorney, Agent, or Firm* — C. A. Whealy

(57) ABSTRACT

A new and distinct cultivar of *Euphorbia* plant named 'Bonpriho', characterized by its upright and mounded plant habit; vigorous growth habit; freely branching habit; medium green-colored leaves; inflorescences with white-colored flower bracts; and good post-production longevity.

1 Drawing Sheet

Botanical designation: *Euphorbia pulcherrima* Willd. ex Klotzsch×*Euphorbia cornastra.*
Cultivar denomination: 'BONPRIHO'.

BACKGROUND OF THE INVENTION

The present invention relates to a new and distinct cultivar of *Euphorbia* plant, an interspecific hybrid botanically known as *Euphorbia pulcherrima* Willd. ex Klotzsch×*Euphorbia cornastra*, and hereinafter referred to by the name 'Bonpriho'.

The new *Euphorbia* plant is a naturally-occurring whole plant mutation of a proprietary selection of *Euphorbia pulcherrima* Willd. ex Klotzsch identified as code number 127, not patented. The new *Euphorbia* plant was discovered and selected by the Inventor as a flowering plant from within a population of plants of the parent selection in a controlled greenhouse environment in Yellow Rock, New South Wales, Australia in March, 2002.

Asexual reproduction of the new *Euphorbia* plant by terminal vegetative cuttings in a controlled greenhouse environment in Yellow Rock, New South Wales, Australia since December, 2002 has shown that the unique features of this new *Euphorbia* plant are stable and reproduced true to type in successive generations of asexual reproduction.

SUMMARY OF THE INVENTION

Plants of the new *Euphorbia* have not been observed under all possible environmental conditions and cultural practices. The phenotype may vary somewhat with variations in environment conditions such as temperature, daylength and light intensity, without, however, any variance in genotype.

The following traits have been repeatedly observed and are determined to be the unique characteristics of 'Bonpriho'. These characteristics in combination distinguish 'Bonpriho' as a new and distinct *Euphorbia* plant:

1. Upright and mounded plant habit.
2. Vigorous growth habit.
3. Freely branching habit.
4. Medium green-colored leaves.
5. Inflorescences with white-colored flower bracts.
6. Good post-production longevity.

In side-by-side comparisons conducted in Yellow Rock, New South Wales, Australia, plants of the new *Euphorbia* differed primarily from plants of the parent selection in flower bract color as plants of the parent selection had pink-colored flower bracts.

Plants of the new *Euphorbia* can be compared to plants of the *Euphorbia pulcherrima*×*Euphorbia cornastra* 'Eckcory', disclosed in U.S. Plant Pat. No. 15,849. In side-by-side comparisons, plants of the new *Euphorbia* differed from plants of 'Eckcory' in the following characteristics:

1. Plants of the new *Euphorbia* had longer and narrower leaves than plants of 'Eckcory'.
2. Inflorescences of plants of the new *Euphorbia* had more flower bracts than inflorescences of plants of 'Eckcory'.
3. Plants of the new *Euphorbia* and 'Eckcory' differed in flower bract color as plants of 'Eckcory' had light red purple-colored flower bracts.
4. Inflorescences of plants of the new *Euphorbia* had more and larger cyathia than inflorescences of plants of 'Eckcory'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet comprises a side perspective view of a typical flowering plant of 'Bonpriho' grown in a container.

The photograph at the bottom of the sheet is a close-up view of typical inflorescences of 'Bonpriho'.

DETAILED BOTANICAL DESCRIPTION

Plants used in the aforementioned photographs and herewith described in detail were grown in 13.5-cm containers during late autumn in a polyethylene-covered greenhouse in Higashiomi, Shiga, Japan and under environmental conditions and cultural practices which approximate those generally used in commercial production. During the production of the plants, day temperatures averaged 23° C. and night temperatures averaged 13° C. Measurements and numerical values represent averages for typical flowering plants. Plants were four months old when the photographs and the description were taken. In the following description, color references are made to The Royal Horticultural Society Colour Chart, Fourth Edition, 2001, except where general terms of ordinary dictionary significance are used.

Botanical classification: *Euphorbia pulcherrima* Willd. ex Klotzsch×*Euphorbia cornastra* 'Bonpriho'.

Parentage: Naturally-occurring whole plant mutation of a proprietary selection of *Euphorbia pulcherrima* Willd. ex Klotzsch identified as code number 127, not patented.

Propagation:

*Type*.—Terminal vegetative cuttings.

*Time to initiate roots, summer*.—About one week at 20° C. to 25° C.

*Time to initiate roots, winter*.—About two weeks at 15° C. to 20° C.

*Time to produce a rooted young plant, summer*.—About three weeks at 20° C. to 25° C.

*Time to produce a rooted young plant, winter*.—About four weeks at 15° C. to 20° C.

*Root description*.—Fibrous; white in color.

*Rooting habit*.—Freely branching; moderately dense.

Plant description:

*Plant habit and form*.—Upright and mounded plant habit; inverted triangle; inflorescences positioned above the foliar plane; vigorous growth habit.

*Plant height*.—About 61 cm.

*Plant diameter or spread*.—About 60.7 cm.

*Lateral branch description*.—Quantity: Freely branching habit, about eight lateral branches develop per plant; pinching is typically not required. Length: About 47.8 cm. Diameter: About 5.1 mm. Internode length: About 3.9 cm. Strength: Strong. Texture: Smooth, glabrous. Color, developing: Close to 144A. Color, mature: Close to N199A to N199B.

*Foliage description*.—Arrangement: Alternate, simple. Length: About 11.7 cm. Width: About 4.6 cm. Shape: Narrowly elliptic. Apex: Acute. Base: Acute to obtuse. Margin: Shallowly serrated. Venation pattern: Pinnate, reticulate. Texture, upper surface: Smooth, glabrous. Texture, lower surface: Scabrous. Color: Developing and fully expanded leaves, upper surface: Close to 143A to 143B; venation, close to 145C. Developing and fully expanded leaves, lower surface: Close to 138A; venation, close to 145C. Petiole: Length: About 3.5 cm. Diameter: About 1.6 mm. Texture, upper and lower surfaces: Smooth, glabrous. Color, upper and lower surfaces: Close to 145A.

Inflorescence description:

*Inflorescence type and habit*.—Inflorescences are compound corymbs of cyathia with colored flower bracts subtending the cyathia; inflorescences positioned above the foliage.

*Quantity of inflorescence*.—One inflorescence develops per lateral branch.

*Fragrance*.—None detected.

*Natural flowering season*.—Plants typically flower during the autumn and winter in Japan; inflorescence initiation and development can also be induced under artificial long nyctoperiod/short photoperiod conditions; early flowering habit, plants flower about 50 days under natural season conditions in Japan.

*Post-production longevity*.—Good post-production longevity; plants of the new *Euphorbia* maintain good substance and bract color for about seven weeks.

*Flower bracts*.—Quantity per inflorescence: About 13. Length, largest bracts: About 5.4 cm. Width, largest bracts: About 2.2 cm. Shape: Narrowly ovate. Apex: Acute. Base: Obtuse. Margin: Shallowly serrate. Texture, upper and lower surfaces: Smooth, glabrous. Aspect: Close to perpendicular to the stem axis. Venation pattern: Pinnate, reticulate. Color: Developing or transitional bracts, upper surface: Close to 154D tinted with close to 27D. Developing or transitional bracts, lower surface: Close to 154D. Fully expanded bracts, upper surface: Close to NN155A slightly blushed with close to 27D; venation, close to 143C and 183D. Fully expanded bracts, lower surface: Close to NN155A. Flower bract petiole: Length: About 9.5 mm. Diameter: About 1 mm. Texture, upper and lower surfaces: Smooth, glabrous. Color, upper and lower surfaces: Close to 145B and 18D.

*Cyathia*.—Quantity per corymb: About nine. Diameter of cyathia cluster: About 1.4 cm. Length, individual cyathium: About 6 mm. Diameter, individual cyathium: About 4 mm. Shape, individual cyathium: Globose. Color: Close to 143B to 143C. Nectaries: Quantity per cyathium: One or two. Size: About 3 mm by 1.6 mm. Color: Close to 154A to 154B.

*Peduncles*.—Length: About 3 mm. Diameter: About 1.2 mm. Strength: Strong. Aspect: Mostly upright. Texture: Smooth, glabrous. Color: Close to 145A.

*Reproductive organs*.—Stamens: Quantity per cyathium: Few. Anther shape: Lanceolate or globose. Anther length: About 1 mm to 3 mm. Anther color: Close to 4D. Amount of pollen: Scarce to none. Pistils: Plants of the new *Euphorbia* do not develop pistils.

*Seed/fruit*.—Seed and fruit production has not been observed.

Disease/pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpriho' as illustrated and described.

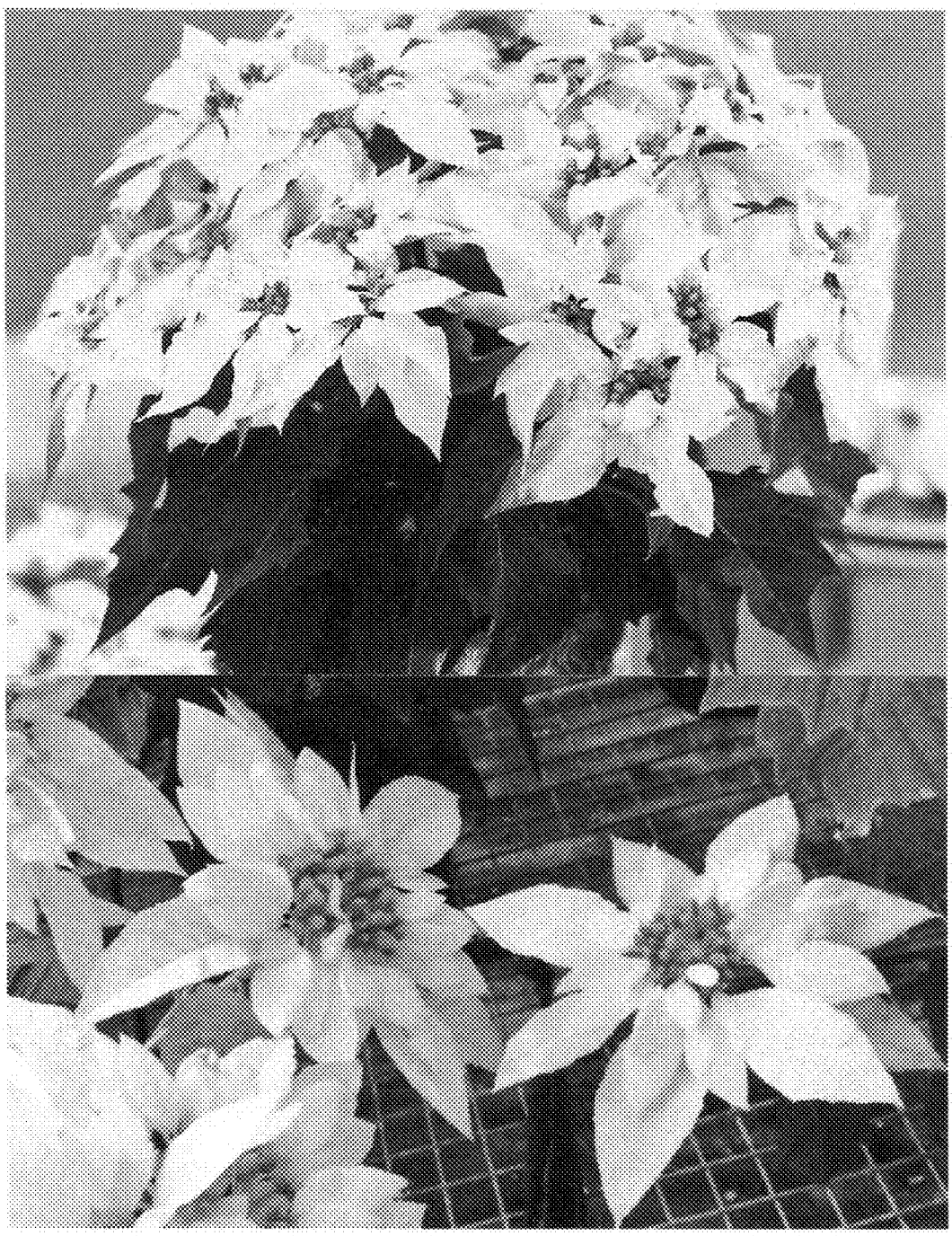

* * * * *